United States Patent
Guittard et al.

[11] Patent Number: 6,036,973
[45] Date of Patent: *Mar. 14, 2000

[54] THERAPY FOR NEUROLOGICAL DISEASES

[75] Inventors: George V. Guittard, Cupertino; Jerry D. Childers, Sunnyvale; Patrick S.-L. Wong, Palo Alto; Fernando E. Gumucio, San Jose; David J. Kidney, Palo Alto, all of Calif.

[73] Assignee: ALZA Corporation, Mountain View, Calif.

[*] Notice: This patent is subject to a terminal disclaimer.

[21] Appl. No.: 08/892,995

[22] Filed: Jul. 15, 1997

Related U.S. Application Data

[63] Continuation-in-part of application No. 08/266,045, Jun. 27, 1994, Pat. No. 5,698,224.

[51] Int. Cl.[7] .......................... A61K 9/00; A61K 31/13; A61K 31/135
[52] U.S. Cl. .................. 424/457; 424/457; 424/468; 424/471; 424/472; 424/473; 424/479; 424/480; 424/482; 424/486; 424/488
[58] Field of Search .................. 424/468, 471, 424/472, 480, 439, 451, 452, 457, 463, 486, 488, 473, 479, 482

[56] References Cited

U.S. PATENT DOCUMENTS

| | | | |
|---|---|---|---|
| 2,799,241 | 7/1957 | Wurster | 118/24 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,327,725 | 5/1982 | Cortese et al. | 128/260 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |
| 4,816,456 | 3/1989 | Summers | 514/255 |
| 4,857,330 | 8/1989 | Stephen et al. | 424/424 |
| 5,698,224 | 12/1997 | Guittard et al. | 424/468 |
| 5,916,925 | 6/1999 | Higuchi et al. | 514/678 |

FOREIGN PATENT DOCUMENTS

| | | |
|---|---|---|
| 0595 365 A1 | 5/1994 | European Pat. Off. . |
| WO 92/15285 | 9/1992 | WIPO . |
| WO 93/24154 | 12/1993 | WIPO . |
| WO 95/03052 | 2/1995 | WIPO . |

OTHER PUBLICATIONS

AR—Preparation of Compressed Tablet Granulations by the Air–Suspension Technique II*, Wurster, Dale E., J. Am. Phar. Assoc., Sci. Ed., vol. 49, pp 82–84 (1960).

AS—Air–Suspension Technique of Coating Drug Particles*, Wurster, Dale E., J. Am. Phar. Assoc., Sci Ed., vol. 48, pp 451–454 (1959).

*Primary Examiner*—Jeffrey C. Mullis
*Attorney, Agent, or Firm*—Paul L. Sabatine; Susan K. Thomas

[57] ABSTRACT

A dosage form is disclosed for administering 10 ng to 1200 mg tacrine to a patient in need of tacrine therapy.

14 Claims, 2 Drawing Sheets

THERAPY FOR NEUROLOGICAL DISEASES

CROSS-REFERENCE TO RELATED APPLICATIONS

This application is a continuation-in-part application of U.S. Ser. No. 08/266,045, filed Jun. 27, 1994 now U.S. Pat. No. 5,698,224 issued Dec. 16, 1997.

FIELD OF THE INVENTION

This invention pertains to therapy indicated for the management of neurological diseases. More particularly, the invention relates to a dosage form that provides a controlled delivery of tacrine over an extended time for the treatment of neurological diseases, including Alzheimer's disease. The invention concerns additionally a therapeutic composition of matter comprising tacrine useful for treating neurological diseases, including Alzheimer's disease. The invention relates further to a method of administering tacrine to produce a beneficial effect for treating neurological diseases, including Alzheimer's disease.

BACKGROUND OF THE INVENTION

The drug tacrine is indicated for the treatment of neurological diseases, including Alzheimer's disease. The neurological-Alzheimer's disease is a progressive, irreversible brain disorder that strikes more frequently with advancing age. The common symptoms of this neurological disease generally include memory loss, confusion, impaired judgment, personality changes, and the loss of language skills. There is, during the course of the disease, a dependence on others to assist the patient in performing tasks such as taking medicine. The average length of the illness is seven years, but it can last fifteen or more years. Presently, research indicates the symptoms of Alzheimer's disease are the result of the loss of nerve cell function in distinct areas of the brain. Alzheimer's disease affects an estimated four-million people, and most cases occur after age sixty; however, the disease affects some individuals in their forties and fifties, usually affecting about ten percent of people over sixty-five. Alzheimer's disease affects all people, and the disease is not restricted to any race, gender, or socioeconomic class.

The drug tacrine for treating neurological diseases, including Alzheimer's disease, is disclosed in U.S. Pat. No. 4,816,456 issued to Summers. The patent teaches the drug tacrine can be administered by standard noncontrolled tablet, pill, powder, elixir, solution, suppository, ointment, cream and capsule, which are dose-dumping conventional forms. The conventional forms deliver the drug by dose-dumping, and this leads to uneven dosing of drug, to uneven blood levels of the drug characterized by peaks and valleys, and accordingly, this does not provide controlled-rate therapy over an extended period of time. Presently, tacrine is administered many times a day because tacrine has a half-life of about three hours. The prior-art dosing patterns and the half-life characteristics of tacrine dictate of the need for an unique dosage form that can administer tacrine over an extended therapeutic time to provide continuous therapy and beneficial therapy to an Alzheimer's patient. The medical history of Alzheimer's disease is known in *Current Therapy*, Conn, pp. 831–835 (1994).

The prior art provided dosage forms that can administer many drugs for extended-controlled therapy. For example, in U.S. Pat. Nos. 3,845,770 and 3,916,899 issued to Theeuwes and Higuchi, in U.S. Pat. No. 4,327,725 issued to Cortese and Theeuwes, and in U.S. Pat. Nos. 4,612,008, 4,765,989, and 4,783,337 issued to Wong, Barclay, Deters and Theeuwes, a dosage form is disclosed that provides therapy by pressure generated inside the dosage form. The dosage form of these patents operates successfully for delivering a drug that develops a high pressure gradient across a semipermeable membrane. The drug tacrine, however, possesses a low osmotic pressure, which dictates against providing an osmotic dosage form for use in the gastrointestinal tract. The gastrointestinal tract has a high osmotic pressure, and this speaks against an osmotic dosage form comprising tacrine as this environment can adversely affect the delivery of tacrine, from the dosage form in this environment.

It is immediately apparent in light of the above presentation that an urgent need exists for a dosage form endowed with the necessary physical-chemical properties for delivering tacrine. The need exists for a dosage form for delivering tacrine at a controlled-rate in a continuous dose in a therapeutic tacrine range governed by the dosage form, while simultaneously providing the beneficial tacrine therapy. It will be appreciated by those versed in the drug dispensing art that if such a dosage form is provided that can administer tacrine in the desired delivery program, the dosage form or a therapeutic composition in the dosage form comprising tacrine would represent an advancement and valuable contribution in Alzheimer therapy.

OBJECTS OF THE INVENTION

Accordingly, in view of the above presentation, it is an object of this invention to provide a dosage form that delivers tacrine for the management of neurological diseases, including Alzheimer's disease.

Another object of the present invention is to provide a dosage form for orally administering tacrine to a patient in need of tacrine at a controlled-rate, in an extended-therapeutic dose, over an extended period of time.

Another object of the invention is to provide tacrine in a rate-controlled, continuous-release dose, to a neurological-disease patient, including an Alzheimer patient, for maintaining a substantially therapeutic tacrine level in the blood as a function of the prolonged-release system.

Another object of the present invention is to provide a dosage form that can deliver orally tacrine in the gastrointestinal environment, and concomitantly substantially reduces and/or substantially eliminates the unwanted influence of the gastrointestinal environment of the delivery of tacrine in the gastrointestinal tract.

Another object of the present invention is to provide an improvement in a dosage form that administers tacrine, wherein the improvement comprises orally delivering tacrine, in an extended-release dose from the dosage form, for predictable and improved therapy to a patient in need of tacrine therapy.

Another object of the invention is to provide a pulsed dose of tacrine, and an extended release dose of tacrine, for the management of neurological diseases, including Alzheimer's disease.

Another object of the invention is to provide a method for administering tacrine by orally administering tacrine in a known dose per unit time, over an extended time to a patient in need of tacrine therapy, while simultaneously substantially avoiding a toxic range of tacrine.

Another object of the invention is to provide a pulsed release and an extended release of at least two different drugs, which slow the progression of Alzheimer's disease.

Another object of the present invention is to provide a therapeutic, solid, orally administrable composition comprising tacrine blended with a tacrine pharmaceutically acceptable, compatible carrier.

Another object of the invention is to provide a dosage form that delivers tacrine and is characterized as clinically practical by reducing tacrine dosing frequency, reducing fluctuation in circulating tacrine levels and increases patient compliance to provide a more uniform tacrine pharmacological response.

Another object of the present invention is to provide a therapeutic composition comprising tacrine and pharmaceutically acceptable polymers manufactured into a dosage form.

Other objects, features and advantages of the invention will be more apparent to those versed in the dispensing art from the accompanying detailed specification, taken in conjunction with the accompanying drawing figures and claims.

BRIEF DESCRIPTION OF THE DRAWINGS

The drawing figures, which are not drawn to scale, are set forth to illustrate various embodiments of the invention. The drawing figures are as follows.

Drawing

Drawing

Drawing

Drawing

Drawing

Drawing

In the drawings and specification, like parts in related figures are identified by like numbers. The terms appearing earlier in the specification and in the description of the drawings, as well as embodiments thereof, are further described in this specification.

DETAILED DESCRIPTION OF THE DRAWINGS

Figure 1:
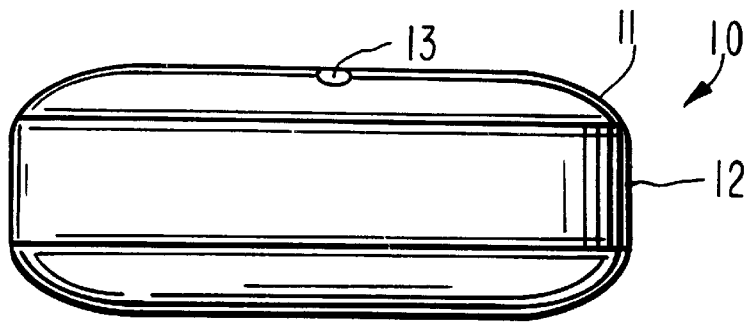
FIG. 1 is a general view of a dosage form designed, shaped and adapted for the oral administration of tacrine at a controlled-rate to a patient in need of tacrine therapy.

Turning now to the drawing figures in detail, which drawing figures are examples of dosage forms provided by this invention, and which examples are not to be construed as limiting, one example of a dosage form is seen in drawing FIG. 1. In drawing FIG. 1, a dosage form 10 is seen, comprising a body member 11, which body member 11 comprises a wall 12 that surrounds and forms an internal area, not seen in drawing FIG. 1. Drawing FIG. 1 comprises at least one exit 13 that connects the exterior of dosage form 10 with the interior of dosage form 10. The dosage form 10 of drawing FIG. 1 illustrates a controlled-release dosage form that delivers tacrine over an extended time. The dosage form, comprising controlled-release, extended-release properties, provided by this invention, is successful at maintaining therapeutic tacrine levels in the blood or in body tissues. The dosage form provided by the invention comprises continuous-extended release of tacrine over a prolonged time. The dosage form provides tacrine blood levels and tissue levels within a therapeutic range optionally below side-effect levels, and above ineffective levels over an extended release time. An extended period of time as used for the purpose of this invention, includes a prolonged period of up to thirty hours over that achieved by conventional drug delivery forms, such as conventional nonrate immediate-release tablets and immediate-release capsules.

Figure 2:
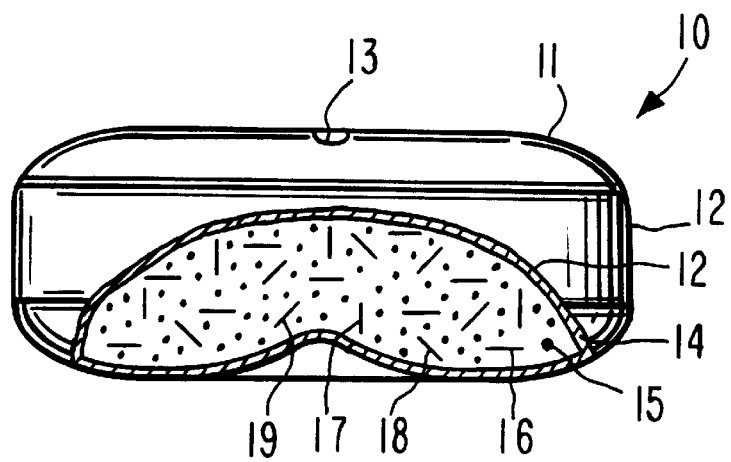
FIG. 2 is an opened view of drawing FIG. 1, depicting the dosage form comprising a pharmaceutical composition comprising tacrine and means for aiding in the delivery of tacrine from the dosage form.

In drawing FIG. 2, dosage form 10 is seen in opened section. In drawing FIG. 2, dosage form 10 comprises a body 11, and a wall 12 that surrounds an internal area or compartment 14. Internal compartment 14 communicates through exit port 13 with the exterior of dosage form 10. Wall 12 of dosage form 10 comprises totally, or in part, a composition that is permeable to the passage of an exterior fluid, such as an aqueous fluid or a biological fluid present in the gastrointestinal tract. Wall 12 is nontoxic, it is inert, and it maintains its physical and chemical integrity during the dispensing time of tacrine. The phrase "maintains its physical and chemical integrity" means wall 12 does not lose its structure, and it does not undergo chemical change during the dispensing of tacrine in the gastrointestinal tract.

Wall 12, as used for all the dosage forms of this invention, comprises a composition that does not adversely effect an animal, a human, or the components of the dosage form. Compositions for forming wall 12 comprise a member selected from the group consisting of a cellulose ester polymer, a cellulose ether polymer, and a cellulose ester-ether polymer. These cellulosic polymers have a degree of substitution, D.S., on the anhydroglucose unit of the cellulose of from greater than 0 up to 3 inclusive. By degree of substitution is meant the average number of hydroxyl groups originally present on the anhydroglucose unit comprising the cellulose polymer that are replaced by a substituting group. Representative of wall-providing polymers comprises a member selected from the group consisting of cellulose acylate, cellulose diacylate, cellulose triacylate, cellulose acetate, cellulose diacetate, cellulose triacetate, mono- di- and tricellulose alkanylates, mono-, di-, and tricellulose alkenylates, mono-, di-, and tricellulose alkinylates, mono-, di-, and tricellulose aroylates. Exemplary polymers include cellulose acetate having a D.S. of up to 1 and an acetyl content of up to 21%, and cellulose acetate having a D.S. of 1 to 2 and an acetyl content of 21 to 35%; and cellulose acetate having a D.S. of 2 to 3 and an acetyl content of 35 to 44.8%. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7; cellulose tricylates having a D.S. of 2.9 to 3, such as cellulose trivalerate, cellulose trilaurate, cellulose tripalmitate, cellulose trisuccinate; and cellulose trioctanoate; cellulose diacylates having a D.S. of 2.2. to 2.6 such as cellulose disuccinate, cellulose dipalmitate, cellulose dioctanoate, and cellulose dipentanoate; and co-esters of cellulose, such as cellulose acetate butyrate and cellulose acetate propionate.

Additional polymers comprising semipermeable properties include acetaldehyde dimethyl cellulose acetate; cellulose acetate ethyl carbamate; cellulose acetate methyl carbamate; cellulose acetate diethyl aminoacetate; semipermeable polyamides; semipermeable polyurethanes; semipermeable sulfonated polystyrenes; semipermeable cross-linked polymers formed by the coprecipitation of a polyanion and polycation as disclosed in U.S. Pat. Nos. 3,173,876, 3,3,276,586 3,541,005, 3,541,006, and 3,546,142; semipermeable polymers, as disclosed by Loeb and Sourirajan in U.S. Pat. No. 3,133,132; semipermeable, lightly cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-8}$ to $2.5 \times 10^{-3}$ ($cm^2/hr.atm$) expressed per atmosphere of hydrostatic or osmotic pressure difference across the semipermeable wall. The polymers are known to the art in U.S. Pat. Nos. 3,845,770; 3,916,899 and 4,160,020; and in *Handbook of Common Polymers*, Scott, J. R. and W. J. Roff, (1971) published by CRC Press, Cleveland, Ohio.

In drawing FIG. 2, dosage form 10, in compartment 14, comprises anti-neurological disease, including anti-Alzheimer's disease, drug tacrine 15, which tacrine 15 is present as a member selected from the group consisting of tacrine base, pharmaceutically acceptable organic salt, pharmaceutically acceptable inorganic salt, including the hydrochloride, hydrobromide, sulfate, phosphate, lactate, citrate, tartrate, malate, maleate, fumarate, ascorbate, gluconate, asparate, salicylate, edisylate, laurate, palmitate, nitrate, borate, acetate and oleate. The amount of tacrine 15 in dosage form 10 is 100 ng to 500 mg, which is delivered over an extended period of 30 minutes up to 30 hours. Tacrine 15 is present in dosage form 10 in individual doses of, for example, 25, 40, 60, 80, 85, 100, 128, 150, 170, 250, 300, 400, and 500 mg dose of tacrine. Internal compartment 14 comprises additionally tacrine compositional-forming means 16 to effect the delivery of tacrine 15. The compositional-forming means 16 are provided by the invention because tacrine 15 has a low osmotic pressure of 10 atmospheres, which leads against incorporating it in, and dispensing tacrine from, an osmotic form, since the osmotic pressure of the gastrointestinal tract is equal to or in excess of 10 atmospheres. This environment leads away from dispensing tacrine 15 from an osmotic dosage form 10. This invention unexpectedly found that tacrine 15 can be delivered from osmotic dosage form 10 by formulating a composition that is a tacrine drug core, which tacrine 15 core generates an osmotic pressure inside dosage form 10, characterized by an osmotic pressure needed for the delivery of tacrine. The drug tacrine 15 has a low osmotic pressure of 10 atmospheres, and it requires means 16 for generating an osmotic pressure inside dosage form 10 greater than the osmotic pressure of the gastrointestinal tract. The osmotic pressure of gastrointestinal tract artificial gastric fluid is about 11 atmospheres, and artificial intestinal fluid is about 9 atmospheres. The low osmotic pressure of tacrine inside the dosage form is insufficient to deliver tacrine unaided from the dosage form at a controlled rate independent of the higher and constantly changing osmotic pressure of the gastrointestinal tract. The physiology of the gastrointestinal tract is influenced by the temporary storage of ingested food as it is reduced to a semiliquid state, the secretion of chemicals and enzymes to assist in ingestion, and contractions of different durations of the gastrointestinal wall, all of which influence the unpredictability of the osmotic pressure of the gastrointestinal tract. The presence of means 16 is for generating an osmotic pressure higher than the gastrointestinal environment. It can be measured by using an osmometer such as a Model 320B, Vapor Pressure Osmometer from the Hewlett-Packard Co., Avondale, Pa. The osmotic pressure $\pi$, is expressed in atmospheres, atm. The osmotic pressure is measured in a commercially available osmometer that measures the vapor pressure difference between water and the solution to be analyzed, and according to standard thermodynamic principles the vapor pressure ratio is converted into osmotic pressure. Another osmometer that can be used for this purpose is the Model 1001-A Knauer Vapor Pressure Osmometer from Utopia Instrumenting, Joliet, Ill. The osmotic pressure is measured as one of the colligative properties of a solution and calibrated in a recorder so that the output, I mVFS, directly gives the osmolality value: 1 osmole/kg water FS according to thermodynamic principles. The values are converted into osmotic pressure. Representative of means 16 are nontoxic compounds that generate an osmotic pressure of 10 atm or greater. Representative of means 16 comprises a member selected from the group consisting of inorganic salt, organic salt, monosaccharide, disaccharide, pentose, hexose, inorganic acid, organic acid, oxide, esters, alcohol, amines and imides, as further exemplified by sodium phosphate monobasic of 28 atm, sodium phosphate dibasic 29 atm, sodium phosphate dibasic 31 atm, sodium phosphate dibasic 31 atm, sodium phosphate tribasic 36 atm, potassium sulfate 39 atm, dextrose 82 atm, glucose 83 atm, sucrose 85 atm, mannitol sucrose combination 170 atm, dextrose sucrose combination 190 atm, mannitol dextrose combination 225 atm, lactose dextrose combination 225 atm, potassium chloride 245 atm, lactose sucrose 250 atm, fructose 355 atm, sodium chloride 356 atm, mannitol fructose 415 atm, sucrose fructose combination 430 atm, dextrose fructose combination 450 atm, and lactose fructose combination 500 atm; and further, means 16 embraces magnesium sulfate, magnesium chloride, lithium sulfate, potassium acid phosphate, inositol, magnesium succinate, tartaric acid, raffinose and sorbitol. The amount of osmotic pressure-generating means 16 present in the tacrine core is 2 to 75 wt %.

The tacrine core composition comprises 0.0 to 20 wt % of a binding agent. In a present manufacture, the drug core comprises 0.25 to 20 wt % of a binding agent represented by a vinyl polymer of 5,000 to 350,000 viscosity-average molecular weight. The vinyl polymers are selected from noncross-linked poly-n-vinylamide, poly-n-vinylacetamide, poly(vinylpyrrolidone), also known as poly-n-vinylpyrrolidone, poly-n-vinylcaprolactone, poly-n-vinyl-5-methyl-2-pyrrolidone, and poly-n-vinylpyrrolidone copolymers, with a member selected from the group consisting of vinyl acetate, vinyl alcohol, vinyl chloride, vinyl fluoride, vinyl butyrate, vinyl laurate and vinyl stearate. The binders include also cross-linked, insoluble polymeric N-vinyl-2-pyrrolidone possessing a molecular weight of 1,000,000 to 7,500,000. The crosslinked polymers are commonly referred to as crospovidone. Representative of other binders are acacia, starch and gelatin.

The therapeutic tacrine composition comprises 0.01 to 10 wt % of a lubricant 18. the lubricants comprise a member selected from the group consisting of stearic acid, magnesium stearate, magnesium oleate, magnesium palmitate, calcium oleate, oleic acid, sodium stearyl fumarate, potassium palmate and caprylic acid. The lubricant is used during manufacture to prevent sticking to manufacturing equipment, including die walls and punch faces.

The therapeutic composition comprises 0 to 20 wt % of a suspending agent 19, and in a present manufacture 0.25 to 20 wt % of suspending agent 19. The suspending agents are represented by cellulose ethers. The cellulose ethers comprise a hydroxypropylalkylcellulose of 9,000 to 250,000 number-average molecular weight, selected from the group consisting of hydroxypropylmethylcellulose, hydroxypropylethylcellulose, hydroxypropylisopropylcellulose, hydroxypropylbutylcellulose, hydroxypropylpentylcellulose, and hydroxypropylhexylcellulose. The cellulose ether comprises hydroxyalkylcellulose of 7,500 to 150,000 viscosity-average number molecular weight, as represented by a member selected from the group consisting of hydroxymethylcellulose, hydroxyethylcellulose, hydroxypropylcellulose, hydroxybutylcellulose, hydroxypentylcellulose, and hydroxyhexylcellulose. The weight of all components in the tacrine composition is equal to 100 wt %.

Figure 3:
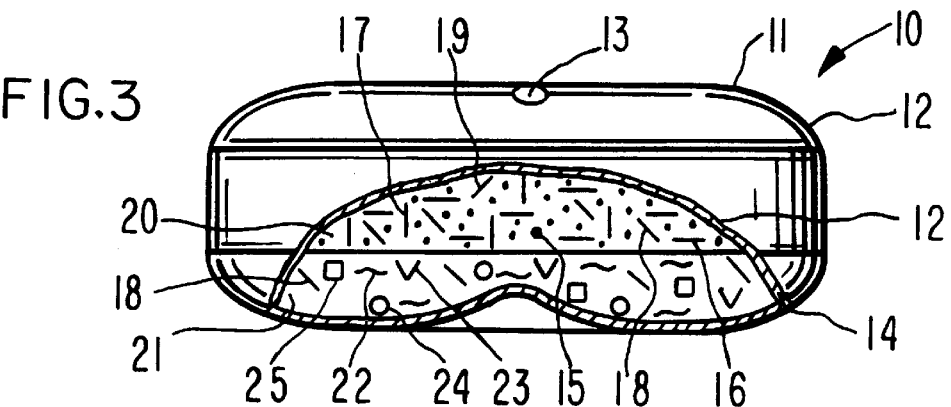
FIG. 3 is an opened view of drawing FIG. 1, illustrating the dosage form comprising a pharmaceutical composition comprising tacrine and displacement compositional means for pushing the pharmaceutical composition containing the tacrine from the dosage form.

In drawing FIG. 3, dosage form 10 is seen in opened section. Dosage form 10 comprises a body 11 and a semipermeable wall 12 that surrounds and defines an internal compartment 14. Internal compartment 14 communicates through exit port 13 with the exterior of dosage form 10. Tacrine 15 is present in a core-layer 20, and layer 20 comprises tacrine 15, osmotic means 16 for generating osmotic pressure in compartment 14, a binding agent 17, a lubricant 18, and a suspending agent 19. Compartment 14 comprises a displacement layer 21. Displacement layer 21 is a push layer that cooperates with tacrine-core layer 20 to successfully deliver tacrine 15 from dosage form 10. Displacement layer 21 comprises an osmopolymer, also known as an osmogel, which imbibes fluid, swells and expands, and thereby occupies space for pushing or displacing the tacrine composition through exit 13 from dosage form 10. The displacement layer 21 comprises 30 to 99 wt % of an osmopolymer. The osmopolymer 22 are represented by poly(alkylene oxide) comprising a 1,000,000 to 10,000,000 molecular weight, such as poly(ethylene oxide), poly (propylene oxide), poly(butylene oxide), poly(pentylene oxide), oxide); and an osmopolymer ) and poly(hexylene oxide); and an osmopolymer 22 in displacement layer 21 comprising a carboxyalkylcellulose of 200,000 to 7,500,000 weight-average molecular weight. Representative carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, potassium carboxyethylcellulose, sodium carboxyalkylhydroxyalkylcellulose, carboxymethylhydroxyethylcellulose, carboxyethylhydroxyethylcellulose and sodium carboxymethylhydroxypropylcellulose.

Displacement layer 21 comprises 0.5 to 40 wt % a fluid-imbibing compound 25 comprising a member selected from the group consisting of an inorganic salt, organic salt, acid, ester, carbohydrate, oxide, magnesium sulfate, magnesium chloride, sodium chloride, lithium chloride, potassium chloride, potassium sulfate, sodium sulfate, sodium sulfite, lithium sulfate, potassium lactate, mannitol, urea, magnesium succinate, tartaric acid, citric acid, lactic acid, raffinose, sorbitol, sucrose, fructose and glucose. The fluid-imbibing compounds are known as osmotically effective compounds, osmotic solutes and osmagents. These osmotic compounds imbibe an environmental aqueous or biological fluid, for example, gastrointestinal fluid, into dosage form 10 for contributing to the delivery kinetics of displacement layer 21. this fluid activity further enables layer 21 to expand and push the tacrine composition from the dosage form.

The displacement layer 21 comprises 0 to 3 wt %, and in a present operation 0.1 to 3 wt %, of a lubricant selected from the group consisting of sodium stearate, potassium stearate, magnesium stearate, stearic acid, calcium stearate, sodium oleate, calcium palmitate, sodium laurate, sodium ricinoleate, and potassium linoleate. Displacement layer 21 comprises 0 to 20 wt % of a hydroxypropylalkylcellulose and/or a hydroxyalkylcellulose. In many manufactures displacement layer 21 comprises 0.01 to 20 wt % of a hydroxypropylalkylcellulose of 9,000 to 375,000 number-average molecular weight, and/or a hydroxyalkylcellulose of 7,500 to 375,000 viscosity-average molecular weight. The hydroxypropylalkylcellulose, and the hydroxyalkylcellulose are manufacturing excipients, and they possess osmotic properties. The total weight of all ingredients is equal to 100 wt %.

Figure 4:
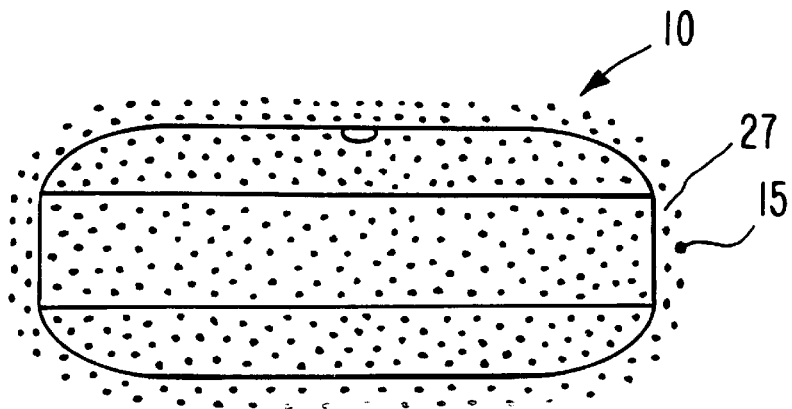
FIG. 4 is a view of the dosage form of drawing FIG. 1 that depicts a pulsed coat on the exterior surface of the dosage form, which coat comprises tacrine and provides a pulsed delivery of tacrine.

Dosage form 10, as seen in drawing FIG. 4, illustrates another manufacture provided by this invention. Dosage form 10 comprises an external coat 27 on the exterior surface of dosage form 10. Coat 27 is an overcoat, and it is a therapeutic composition that delivers a pulse dose from the exterior surface. Overcoat 21 comprises 1 to 125 mg of a member selected from tacrine 15 and its pharmaceutically acceptable salts. The overcoat comprises also pulse doses, represented by 15 mg of tacrine, 22.5 mg of tacrine, 30 mg of tacrine, or 40 mg of tacrine. The pulse dose is released instantly when contact by a biological fluid. The pulsed-release of tacrine is followed by an extended-release of tacrine by dosage form 10. Representative of pulsed-release, extended-release comprise 15 mg pulsed-released dose of tacrine followed by 85 mg extended-release dose of tacrine over 24 hours; 22.5 mg pulsed-release dose of tacrine followed by 127.5 mg extended-release dose of tacrine; and 30 mg pulsed-release dose of tacrine followed by 170 mg extended-release dose of tacrine.

Dosage form 10, as seen in FIG. 4, can comprise the tacrine in the overcoat and tacrine in the dosage form. Dosage form 10 can comprise also a different drug in the overcoat for the treatment of Alzheimer's disease. Representative of these drugs comprise a member selected from the group consisting of aniracetam, bifemelane, phosphatidylserine, pramiracetam, physostigmine, fampridine, linopirdine, selegiline, nimodipine, propentofylline, relnacrine, alpha-tocopherol, aminopyridone, cytisine, 1-hydroxy-tacrine, 9-amino-3,4-dihydroaridine, estrogen, and donepezil.

The therapeutic composition 27, as seen in FIG. 4, comprises tacrine blended with a pharmaceutically acceptable carrier, which carrier is a tacrine-releasing carrier in aqueous, including biological fluids. The carrier comprises 1 to 125 mg of a member selected from the group consisting of alkyl cellulose, hydroxyalkylcellulose, hydroxypropylalkylcellulose, pectin, locus bean gum, gum tragacanth, guar gum, carrageenan, acacia, alginate, xanthan gum, and agar, which gums possess a 5,000 to 4,000,000 number-average molecular weight. Therapeutic composition 27, in another manufacture, comprises 0.25 to 17.5 mg of polyethylene glycol of 100 to 5,000 viscosity-number average molecular weight. The polyethylene glycol functions as a binder in the overcoat. The polyethylene glycol as used herein does not include polyethylene oxide. Therapeutic composition 27 optionally comprises 0.25 to 17.5 mg of acetylated triglyceride. Therapeutic composition 27 provides a dose amount of tacrine as composition 27 dissolves or undergoes dissolution in the gastrointestinal tract in the presence of gastrointestinal fluid of a tacrine receiving patient. Coat 27 provides pulsed tacrine instantly and up to 1 hour of tacrine on entrance of the dosage form into the gastrointestinal tract.

Figure 5:
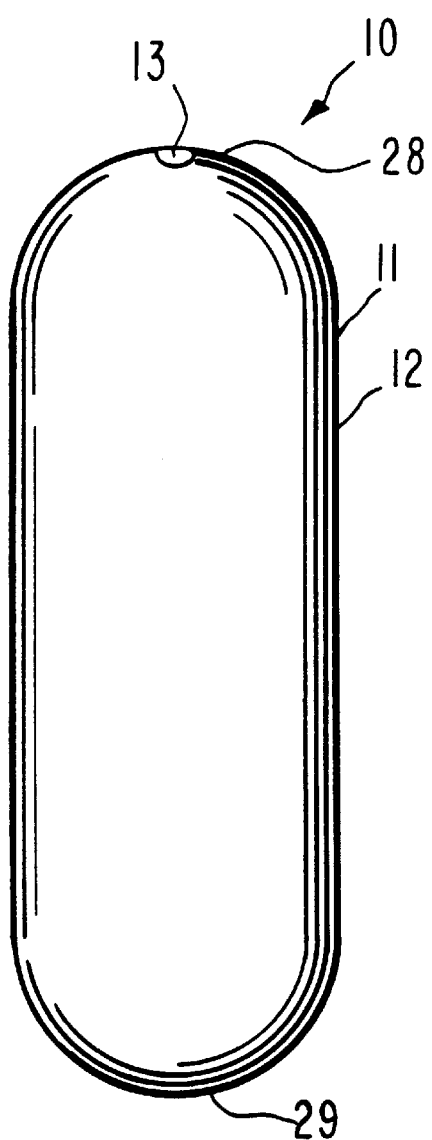
FIG. 5 illustrates the dosage form manufactured as a caplet comprising a continuous body with a pair of curved-rounded ends, for increasing the dose of tacrine delivered, and for increasing the swallowability of the dosage form caplet.

Drawing FIG. 5 illustrates dosage form 10 designed, shaped and adapted as a caplet for orally administering tacrine to a patient, for slowing the progression of Alzheimer's disease. In drawing FIG. 5, dosage caplet 10 comprises a body 11, a wall 12, a passageway 13, a lead end 28 and a trailing, or rear end 29. Caplet 10 can administer tacrine alone, or optionally with another anti-Alzheimer's medication. Caplet 10 can comprise tacrine, and, optionally, selegiline, vitamin E and donepezil. The therapy can be administered as a therapeutic pair, for example, tacrine and selegiline, tacrine and vitamin E, tacrine and estrogen, and tacrine and donepezil.

Figure 6:
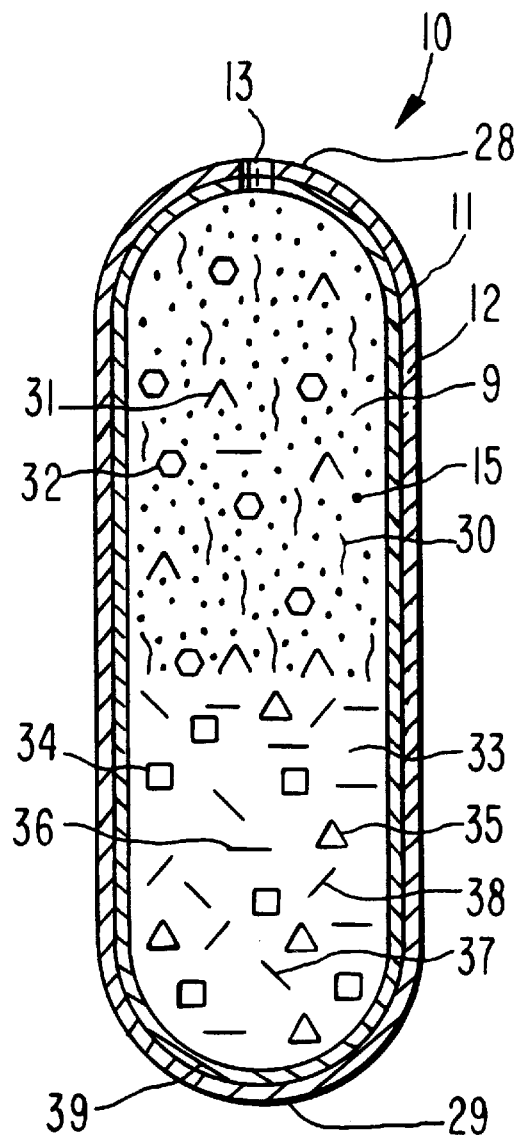
FIG. 6 illustrates the dosage form caplet of drawing FIG. 5 in opened section provided with an outer semipermeable wall and an inner wall, comprising gelatin with the caplet comprising tacrine and means for delivering tacrine from the dosage form.

Drawing FIG. 6 illustrates dosage form 10 of drawing FIG. 5 in opened section. In drawing FIG. 6, dosage form 10 comprises a caplet shape adapted and sized for oral admittance into the gastrointestinal tract of a human. The dosage form caplet is illustrated for delivering the maximum dose of tacrine 15. The dosage form caplet 10 substantially delivers 100% of tacrine from dosage caplet 10. Dosage caplet 10 comprises a single unit body 11, comprising a lead end 28 and a rear end 29, which in one embodiment are round or oval shaped to increase delivery of tacrine 15 and for ease of oral administration. Dosage form 10 comprises a semipermeable wall 12 that surrounds an internal compartment 14. Semipermeable wall 12 is permeable to the passage of a fluid, an aqueous or biological fluid present in an environment of use, such as an animal, including a human. The semipermeable wall 12 is nontoxic, substantially inert, and it maintains its physical and chemical integrity during the tacrine-dispensing life of dosage caplet 10.

Compartment 14 comprises a tacrine composition present as a tacrine layer 9, comprising 100 ng to 500 mg of a member selected from the group consisting of tacrine and its pharmaceutically acceptable salt. The tacrine layer 9 can comprise optionally 100 to 500 mg of a tacrine-supporting drug for treating neurological diseases, selected from the group consisting of aniracetam, bifemelane, phosphatidylserine, pramiracetam, physostigmine, fampridine, linopirdine, selegiline, nimodipine, propentofylline, reinacrine, alpha-tocopherol, aminopyridine, cytisine, estrogen, 1-hydroxy-tacrine, and 9-amino-3,4-dihydroacredine. In a manufacture wherein the dosage form comprises two anti-Alzheimer's drugs, the total dose in dosage form 10 is 200 ng to 500 mg of drug.

Compartment 14 comprises 20 to 350 mg of an osmopolymer 30, selected from the group consisting of alkali carboxyalkylcellulose, sodium carboxymethylcellulose, potassium carboxymethylcellulose and sodium carboxyethylcellulose of 25,000 to 175,000 molecular weight; a polyalkylene oxide of 75,000 to 750,000 molecular weight comprising a member selected from the group consisting of polyethylene oxide, polypropylene oxide, polyisopropyline oxide, polybutylene oxide, polypentylene oxide, and polyhexylene oxide, which polyalkylene oxides perform as osmogels, that is, hydrogels with osmotic properties thereby distinguished from water-soluble polyethylene glycols; 1 to 120 mg of an alcohol 31 of the formula $(CH_2OH)(CHOH)_n(CH_2OH)$, wherein n is 2 to 5 as represented by sorbitol, mannitol and malititol, 0.01 mg to 30 mg of a binding agent 32 selected from the group consisting of poly(vinyl pyrrolidone), poly(vinyl carbazole), poly(vinyl pyridine), poly(vinyl oxazole), poly(vinyl methyloxozolidone), poly (vinyl formyl), copolymer of polyvinylpyrrolidone with vinyl acetate, copolymer of polyvinylpyrrolidone and vinyl alcohol, copolymer of polyvinylpyrrolidone with vinyl chloride, copolymer of polyvinylpyrrolidone with vinyl fluoride, copolymer of polyvinylpyrrolidone with vinyl butyrate, copolymer of polyvinylpyrrolidone with vinyl laurate, copolymer of polyvinylpyrrolidone with vinyl stearate, and poly(vinyl butyrol) of 5,000 to 350,000 viscosity-average molecular weight; and 0.025 mg to 5 mg of a lubricant selected from the group consisting of calcium stearate, magnesium stearate, sodium stearate, potassium stearate, stearic acid, potassium oleate, potassium laurate, and sodium linoleate. A colorant or dye can be present in compartment 14 for aiding in identifying tacrine 16 present in osmotic caplet 10.

Osmotic dosage caplet 10 comprises a displacement or expandable driving layer 33 that imbibes fluid and increases in volume thereby operating to push the tacrine composition through exit passageway 13 from dosage caplet 10. Displacement layer 33 comprises 20 to 375 mg of an osmotic fluid-imbibing hydrogel 34 selected from the group consisting of alkali carboxyalkylcellulose, carboxymethylcellulose, sodium carboxymethylcellulose, potassium carboxymethylcellulose, sodium carboxyethylcellulose, sodium carboxypropylcellulose, calcium carboxymethylcellulose, potassium carboxyisopropylcellulose, sodium carboxymethylethylcellulose, and sodium carboxymethylhydroxyethylcellulose having a 200,000 to 7,500,000 viscosity-average molecular weight; a polyalkylene oxide of 1,000,000 to 10,000,000 molecular weight selected from the group consisting of polyethylene of 1,000,000 molecular weight and a 2% concentration exhibiting a viscosity at 25° C. of cps of 400–800; a polyethelene oxide of 2,000,000 molecular weight, exhibiting a viscosity at 25° C. of 2,000 to 4,000 cps; a polyethylene oxide of 4,000,000 molecular weight with a 1% concentration is aqueous fluid exhibiting a viscosity at 25° C. of 1,650 to 5,000 cps; a polyethylene oxide of 7,000,000 molecular weight and a polyethylene oxide of 7,500,000 molecular weight; 5 to 100 mg of an osmotic aqueous imbibing compound 35, selected from the group consisting of salt, monosaccharide, disaccharide, ester, acid, ether, amide, imide, and oxide; 0 to 30 mg of a hydroxyalkylcellulose 36, comprising a 7,500 to 150,000 viscosity-average molecular weight; 1 to 75 mg of a hydroxypropylalkylcellulose 37 comprising a 9,200 to 250,000 molecular weight; 0.01 to 3.0 mg of a lubricant 38; and 0 to 2 mg of a colorant; such as ferric oxide.

Dosage caplet 10, in another manufacture, comprises an inner coat 39. Coat 39 surrounds the tacrine composition layer 9 and the displacement layer 33. Coat 39 is positioned between the inside surface of wall 12, in contact with both inside wall 12, layer 9, and layer 33. Coat 39 comprises a coat-forming fluid permeable composition selected from the group consisting of 100 wt % gelatin having a viscosity of 10 to 40 centipoise and a bloom value of 160 to 250; a coat comprising 60% to 99 wt % gelatin and 1 to 40 wt % of a polysaccharide selected from the group consisting of agar, acacia, karaya, tragacanth, algin and guar; and a coat comprising 40 to 80 wt % hydroxypropylcellulose and 20 to 50 wt % hydroxypropylalkylcellulose, represented by hydroxypropylmethylcellulose. The total weight of all components in coat 39 is equal to 100 wt %.

The phrases "controlled-release" and "extended-release" as used herein indicate that control is exercised over both the duration and the profile of the tacrine-release pattern. The expression "passageway" as used for the purpose of this invention includes aperture, orifice, bore, pore, porous element through which the tacrine can be pumped, diffuse, travel or migrate, a hollow fiber, capillary tube, porous overlay, porous insert, microporous member, and porous composition. The expression also includes a passageway formed by a compound that erodes or is leached from wall 12 in the fluid environment of use, to produce at least one passageway 13 in dosage form 10. Representative compounds suitable for forming at least one passageway, or a multiplicity of passageways, includes an erodible poly (glycolic) acid or poly(lactic) acid member in the wall; a gelatinous filament; a water-removable poly(vinyl alcohol); and leachable compounds such as fluid removable pore-forming polysaccharides, acids, salts, or oxides. A passageway or a plurality of passageways can be formed by leaching a compound such as sorbitol, sucrose, lactose, fructose or the like from the wall to provide a controlled-release dimensioned pore-passageway. The passageway can have any shape, such as round, triangular, square, elliptical, and the like, for assisting in the controlled-metered release of tacrine from dosage form 10. Dosage form 10 can be constructed with one or more passageways in spaced apart relation to one or more surfaces of a dosage form 10. Passageway 13 and equipment for forming passageways are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled releasing dimension, sized, shaped and adapted as a releasing-pore formed by aqueous leaching of a compound to provide a releasing-pore of controlled release-rate are disclosed in U.S. Pat. No. 4,200,098 by Ayer and Theeuwes; and in U.S. Pat. No. 4,285,987 by Ayer and Theeuwes.

Wall 12 is manufactured in one process by an air suspension process. This process consists in suspending and tumbling a compressed tacrine core comprising a single layer as seen in the above figures, or a bilayer core, as seen in the above figures, in a current of air and wall forming composition until a wall is applied to the dosage form compartment. The air suspension procedure is well suited for independently forming the wall. The air suspension procedure is described in U.S. Pat. No. 2,799,241; *J Am Pharm Assoc.*, Vol. 48, pp. 451–454 (1959); and ibid., Vol. 49, pp. 82–84 (1960). Dosage form 10 can be coated also with a wall-forming composition in a Wurster® air suspension coater, using, for example, methylene dichloride-methanol cosolvent, 80:20, wt:wt; an ethanol-water; or acetone-water cosolvent, for example, 95:5 wt:wt using 2.5 to 4% solids. An Aeromatic® air suspension coater using a methylene dichloride-methanol cosolvent for example, 80:20 wt:wt, can be used for applying wall 12. Other wall forming techniques such as a pan-coating system, wherein wall forming compositions are deposited by successive spraying of the composition on the drug-core compartment, accompanied by tumbling in a rotating pan. Finally, the wall-coated compartments are dried in a forced air over at 30 to 50° C. for up to a week to free dosage form 10 of solvent. Generally, the walls formed by these techniques have a thickness of 1 to 30 mils (0.0254 to 0.762 mm).

Dosage form 10 of the invention is manufactured by standard manufacturing techniques. For example, in one manufacture the tacrine and other core-forming ingredients comprising a single drug layer or bilayer tacrine-displacement core with the tacrine layer facing the exit means 13 are blended and pressed into a solid layer, or a solid bilayer. The tacrine and other ingredients can be dry-blended or blended with a solvent and mixed into a solid or semi-solid formed by convention methods such as ballmilling, calendaring, stirring, roll-milling or churning and then pressed into a preselected shape adopted for use in the gastrointestinal tract. The layer possesses dimensions that correspond to the internal dimensions of the area the layer is to occupy in the dosage form, and in a bilayer dosage form it also possesses dimensions corresponding to the second layer for forming a contacting arrangement therewith. Next, in a bilayer core, the push layer is placed in contact with the tacrine layer. The push layer is manufactured using techniques for providing the tacrine layer. The layering of the tacrine layer and the push layer can be fabricated by convention press-layering techniques. Finally, a single tacrine layer or the two tacrine displacement layer compartment forming members are surrounded with an outer wall. A passageway is laser drilled through the wall. The dosage form is optically oriented automatically by the laser equipment for forming the passageway on the preselected surface for forming the passageway.

In another manufacture, dosage form 10 is manufactured by a wet granulation technique. Granulation is a process of size enlargement, whereby small particles are gathered into larger aggregates in which the original particles can still be identified as reported in *Encyclopedia of Pharmaceutical Technology*, Vol. 7, pp. 121–160 (1993). In a wet granulation technique, for example, tacrine and the ingredients comprising the tacrine-forming layer are blended using poly (vinylpyrrolidone) added to a solvent, such as ethyl alcohol-water 98:2 v:v (volume: volume), as the granulation fluid. Other granulating fluid, such as denatured alcohol 100%, can be used for this purpose. The ingredients forming the tacrine layer are individually passed through a mesh screen, usually 40 mesh, and then thoroughly blended in a mixer. Next, other ingredients comprising the tacrine layer are dissolved in a portion of the granulation fluid, such as the cosolvent described above. Then, the latter prepared wet blend is slowly added to the tacrine blend with continual mixing in the blender. The granulating fluid is added until a wet blend is produced, which wet mass then is forced through a 20-mesh screen onto oven trays. The blend is dried for 18 to 24 hours at 30 to 50° C. The dry granules are then sized, then usually with a 20-mesh screen. Next, a lubricant is passed through a screen, such as an 80-mesh screen, and added to the dry screen granule blend. The granulation is placed in a blender and blended for 1 to 10 minutes. A push layer is made by the same wet granulation techniques. The compositions are compressed into their individual layers as a bilayer core in a layer press.

Another manufacturing process that can be used for providing the compartment-forming composition layers comprises blending the powdered ingredients for each layer independently in a fluid bed granulator. After the powders are dry blended in the granulator, a binder fluid, for example, poly(vinylpyrrolidone) in water, or in denatured alcohol, or in 95:5 ethyl alcohol/water, or blends of ethanol and water, is sprayed on the powders. Optionally, the ingredients can be dissolved or suspended in the granulating fluid. The granules are then dried in the fluid-bed granulator. This process granulates all the ingredients present therein while adding the granulating fluid. After the granules are dried and discharged from the fluid bed granulator, a lubricant such as stearic acid or magnesium stearate is added to the granulator. The granules for each separate layer are compressed into bilayer cores in the manner described above.

Dosage form 10 of the invention can be manufactured by mixing tacrine with composition-forming ingredients and pressing the composition into a layer possessing dimensions that correspond to the internal dimensions of the compartment of dosage form 10. In another manufacture, the tacrine and other tacrine composition-forming ingredients and a solvent are mixed into a solid, or a semisolid, by conventional methods, such as ballmilling, shaking, calendaring, tumbling, stirring or rollmilling, and then pressed into a preselected layer-forming shape. Next, a layer of a composition comprising an expandable hydrogel and an optional, fluid-imbibing compound are placed in contact with the tacrine layer. The layering of the first layer comprising tacrine and the second layer comprising the osmopolymer-hydrogel and an optional fluid imbibing compound can be accomplished by using a conventional layer press technique. The wall can be applied by molding, brushing, spraying or dipping the pressed bilayer's shapes with wall-forming materials. Another technique that can be used for applying the wall is the air-suspension coating procedure. This procedure consists in suspending and tumbling the two contacting layers in a current of air solution spray until the wall-forming composition surrounds the layers. The air suspension procedure is described in U.S. Pat. No. 2,799, 241; *J Am Pharm Assoc.*, Vol. 48, pp. 451–454 (1979); and ibid., Vol. 49, pp. 82–84 (1960). Other standard manufacturing procedures are described in *Modern Plastics Encyclopedia*, Vol. 46, pp. 62–70 (1969); and in *Pharmaceutical Sciences*, by Remington, 14th Ed, pp. 1626–1678 (1970), published by Mack Publishing Co, Easton, Pa.

The present invention manufactures a dosage form caplet 10 by surrounding a pressed solid caplet-shaped solid body 11 with a semipermeable wall 12, or first with inner coat 39 followed by a semipermeable wall 12. One method of manufacture comprises inserting a pressed body into a caplet channel machine leaving one end exposed, which is dipped into wall-forming bath to coat the exposed end, followed by dipping the other uncoated end into the bath to surround the end with a wall-forming composition. In one manufacture, the caplet is coated with a semipermeable wall and then permitted to dry with rotation for evenly spreading the wall-forming semipermeable wall around the body of the caplet. In another manufacture, a subcoat is applied to the body of the caplet. Next, after the caplet is permitted to dry it is followed by coating the body of the caplet in a semipermeable wall-forming bath. Inner coat 39, in this manufacture, serves as a lubricating coat to facilitate high drug loading of caplet 10 and to facilitate the uninhibited delivery of tacrine 16 from dosage form caplet 10. That is, by lubricating wall 12, it substantially eliminates internal resistance of tacrine delivery from caplet 10.

Another manufacture comprises filling a caplet die with the composition to be compressed into a shape corresponding to the die cavity, and then removing the compressed body from the cavity. The die cavity is lubricated prior to filling the cavity to prevent sticking and to make it easy to remove the compressed caplet-shaped body from the die cavity. The die cavity may be lubricated with a lubricant such as stearic acid, magnesium stearate, calcium stearate, sodium lauryl sulfate or potassium lauryl sulfate. Next, the caplet body is surrounded with a wall. A wall can be applied by using standard wall-coating equipment. Equipment that can be used for coating the compressed body include standard equipment such as the Accela-Cota® coater, High-Coater® coater or the Wurster® suspension coater. The coaters comprise a vaporizer to facilitate drying, and an exhaust system designed to remove solvent vapors and any possible dust. The coating can be effected by using spray guns and atomizing equipment to introduce a wall-forming solution into a coating pan, or to introduce a wall-forming solution into an air suspension column. Optionally, cold or warm air can be introduced into the spraying cycle to regulate the coating and/or drying of the coated caplet. The coating solution can be applied by using a peristaltic spray pump or a pneumatic displacement pump in continuous or interrupted spray and dry patterns. The coating composition is sprayed to a preselected desired thickness, usually 0.01 to 5 mm for each separate wall.

Another manufacture that can be used for coating a pressed caplet body previously pressed in a plate process, rotary die process, reciprocating die process, continuous rotary press, high pressure station rotary press, or high pressure station rotary press, in one manufacture comprises placing a caplet-forming film over a lower mold with the caplet-forming formulation poured onto the film. Then, a film of a wall-forming composition is placed over the caplet body, followed by the top mold. The mold is placed under a press and pressure applied with or without heat to form the caplet. The caplet can be made with a passageway. The passageway is formed integrally by the mold set equipped with a passageway-forming area that prevents coating in the passageway area.

Another manufacture of caplet 10, is manufactured by standard granulation techniques. For example, the caplet-forming ingredients are formulated by the wet granulation technique using an organic cosolvent, such as isopropyl alcohol-methylene dichloride, 80:20, v:v, (volume:volume) as the granulating fluid. The ingredients forming the caplet comprising tacrine and other caplet-forming ingredients are individually passed through a 40-mesh screen and then thoroughly blended in a blender. The screens used herein are U.S. Standard Sieves. Next, a polymer, for example, poly (vinylpyrrolidone), is dissolved in a portion of granulation fluid in the cosolvent described above. Then, the poly (vinylpyrrolidone) solution is slowly added to the dry powder blend with continual mixing in a blender. The granulation fluid is added until a wet blend is produced, generally about 400 cc of granulating fluid per kilogram of blend. The wet mass blend then is forced through a 16 to 30 mesh screen onto trays and dried for 18 to 30 hours at 40 to 60° C. The dried granules are sized with a 20-mesh screen. Next, a lubricant, such as magnesium stearate passed through an 80-mesh screen, is added to the dry screened granular blend and blended for 1 to 5 minutes.

In another process, other caplet-forming compositions are blended in a fluid bed granulator. After the powders are dry blended, a granulation fluid comprising an aqueous granulation fluid is sprayed onto the powders and dried in the granulator. This process granulates all of the ingredients together, while adding the granulation solution. After the granules are dried, a lubricant such as magnesium stearate is added to the granulation. The caplet-forming blend, in either of the above processes, is then pressed into a caplet using a tablet press. The speed of the press is set optionally at 30 rpm, and the maximum load set at 0.5 to 20 tons. Then, the caplet body is surrounded with a wall. The dosage form caplet, in another manufacture, is made by mixing tacrine with fluid-imbibing compound and/or a hydrogel, and pressed into a solid possessing dimensions that correspond to the internal dimensions of the caplet; or, tacrine and other caplet formulation forming ingredients and a solvent are mixed by conventional methods, such as ballmilling, calendaring, stirring or rollmilling, and then pressed into a preselected shape. Next, a layer of a composition comprising a fluid-imbibing compound and/or a hydrogel is placed in contact with a layer of tacrine formulation, and then the two contacting layers, except for a caplet mouth, are surrounded with a semipermeable wall. The wall can be applied by protecting the caplet orifice to keep it open and free from coating by a semipermeable wall-forming material. The wall can be applied by molding, spraying, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds the two, pressed compositions. The air suspension procedure is described in U.S. Pat. No. 2,799,241; *J Am Pharm Assoc.*, Vol. 48, pp. 451–59 (1979); and ibid., Vol. 49, pp. 82–84 (1960). Other standard manufacturing procedures are described in *Modern Plastics Encyclopedia*, Vol. 46, pp. 62–70 (1969); and in *Pharmaceutical Sciences*, by Remington 14th Ed, pp. 1626–1978 (1970), published by Mack Publishing Co., Easton, Pa.

Exemplary solvents suitable for the manufacturing process include inert inorganic and organic solvents that do not adversely harm the materials and the final dosage form. The solvents broadly include members selected from the group consisting of aqueous solvents, alcohols, ketones, esters, ethers, aliphatic hydrocarbons, halogenated solvents, cycloaliphatic hydrocarbons, halogenated solvents, cycloaliphatics, aromatics, heterocyclic solvents, and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naphtha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention, and they should not be considered as limiting the scope of the invention in any way, as these examples and other equivalents thereof will become apparent to those versed in the art in the light of the present disclosure, the drawings, and the accompanying claims.

Example 1

A dosage form is manufactured for orally dispensing tacrine to the gastrointestinal tract of a human patient. The dosage form for dispensing tacrine to the gastrointestinal tract is unexpected, as tacrine has a low osmotic pressure that is substantially equivalent to the normal osmotic pressure of 8 plus atmospheres of the gastrointestinal tract. The osmotic pressure of the gastrointestinal tract is unpredictable and variable, attributed to diet, health and peristaltic mobility. Thus, a dosage form provided by this invention must develop an internal osmotic pressure greater than the osmotic pressure of the gastrointestinal tract, which, for this invention, is at least 10 atmospheres or higher in the dosage form, to provide a controlled rate of delivery of tacrine over a prolonged time. This invention effects an internal osmotic pressure of 10 atmospheres or more by blending tacrine, for example tacrine hydrochloride, with a fluid-imbibing, osmotically effective compound possessing an osmotic pressure gradient across a semipermeable wall of 10 atmospheres or more, for example, mannitol, to provide a combined tacrine hydrochloride fluid imbibing composition of 20 atmospheres. The mutual solubilities of tacrine hydrochloride and fluid imbibing mannitol, which has an osmotic pressure of 40 atmospheres, exhibited an unsuspected osmotic pressure of 58 atmospheres. The mutual solubilities of tacrine-fluid imbibing osmotic pressure generating compound in water at 37° C. at saturation, are in one embodiment in a ratio of 1:1 by weight, or a molar ratio of 0.72:1. The invention prepares an osmotic core formulation by combining tacrine, presently tacrine hydrochloride monohydrate, with the osmotic pressure generating compound mannitol in a 1:1 ratio by weight to produce a homogenous blend. The blend is converted into a wet granulation by wetting the blend with a binding composition comprising poly(vinylpyrrolidone) and ethanol. The fresh mass is passed through a 20-mesh screen and oven dried at 50° C. overnight. Next, the dry granules are passed through a 20-mesh screen and a lubricant, magnesium stearate, is added to the dry granules and blended for an additional 5 minutes. The composition is compressed into single layer tacrine cores to provide the two separate core formulations: (1) a core comprising 86.15 mg of tacrine hydrochloride, 86.15 mg of mannitol, 7.25 mg of poly(vinylpyrrolidone) and 1.81 mg of magnesium stearate; and (2) a core comprising 65.24 mg of tacrine hydrochloride monohydrate, 65.24 mg of mannitol, 3.47 mg of poly(vinylpyrrolidone), 0.69 mg of hydroxypropylmethylcellulose and 4.16 mg of magnesium stearate.

Next, a semipermeable wall is coated around the individual, separate cores. The semipermeable wall forming composition comprises 80 wt % cellulose acetate having a 39.8% acetyl content and 20 wt % poly(vinylpyrrolidone). The cores are coated in a 305 mm pan. The final semipermeable wall coated cores are dried for 18 hours at 45° C. in a light current of air. An exit passageway is drilled through the semipermeable wall connecting the tacrine with the exterior of each dosage form. The exit port has a diameter of 30 mils (0.76 mm) and each dosage form dispenses tacrine for 24 hours.

Example 2

The dosage form of Example 1 is manufactured with a dose of tacrine coated on the exterior surface of the semipermeable wall. The dose of tacrine on the exterior wall comprises a pulsed dose of 15 mg of tacrine.

Example 3

A dosage form adapted, designed and shaped as an osmotic tacrine dosage form is manufactured as follows: first, 3,290 g of tacrine hydrochloride and 3,290 g of mannitol are added to a Freund Flow-Coater bowl, a fluid bed granulator. The bowl is attached and the granulation process is initiated. Next, the dry materials are air suspended and mixed for 7 to 8 minutes. Then, a solution prepared by dissolving 175 g of poly(vinylpyrrolidone) having a molecular weight of 40,000 in 260 g of distilled water is sprayed onto the materials. The blending conditions are monitored during the process of spraying the aqueous poly (vinylpyrrolidone) at a solution spray rate of 125 g/min with an inlet temperature of 45° C. and an air flow of 1,000 cfm. Next, the granules are blended with 35 g of hydroxypropylmethylcellulose and 210 mg of magnesium stearate and the granulation transferred to a Rotocone mixer and mixed to provide homogenous granules.

Next, a hydrogel expansion composition is prepared as follows: first, 950 g of pharmaceutically acceptable poly (ethylene oxide) comprising a 5,000,000 molecular weight, 35 g of microcrystalline cellulose, 25 g sodium chloride, 5.15 g hydroxypropylcellulose of 50,000 molecular weight, 5.15 g of hydroxypropylmethylcellulose of 11,200 molecular weight, and 1.44 g of ferric oxide are blended with all the ingredients and separately screened through a 40-mesh screen. Then, all the materials are transferred to a mixer and mixed for 5 minutes. Then, 400 ml of denatured ethyl alcohol is added to the mixed powders in the mixer and the mixing continued for 3 minutes. The homogenous mixed mass is passed through a 16-mesh screen and allowed to dry at room temperature for 16 hours and then rescreened through a 20-mesh screen. The screened granulation is mixed with 2.5 g magnesium stearate in a roller mill for 6 minutes.

Next, the tacrine composition and the hydrogel composition are compressed into a bilayer core. First, 420 mg of the tacrine composition is added as a first layer to a punch and tamped, then 215 mg of the hydrogel composition is added as a second layer to the punch. The layers are compressed under a compression force of two tons into contacting, layered arrangement.

Then, the bilayered cores are surrounded with a semipermeable wall. The wall-forming composition comprises 60 wt % cellulose acetate having a 39.8% acetyl content, 25 wt % hydroxypropylcellulose having a 18,500 molecular weight, and 15 wt % polyethylene glycol 3,350. The wall-forming composition is dissolved in an acetone: methanol (80:20 wt:wt) cosolvent to make 4.5% solids solution. The wall-forming composition is sprayed onto and around the bilayer cores in a 24 inch (60 cm) Vector® Hi-Coater.

Next, two 25-mil (0.635-mm) exit passageways are drilled through the semipermeable wall to connect the tacrine layer with the exterior of the dosage form. The residual solvent is removed by drying for 48 hours at 50° C. and 50% humidity. Next, the dosage forms are dried a minimum of 4 hours at 50° C. to remove excess moisture. The dosage form, on oral admittance into the gastrointestinal tract, provides tacrine to an Alzheimer patient.

The dosage form provided by this invention is unexpected, as tacrine experimentally exhibits a low osmotic pressure. The solubility of tacrine at 37° C. in water is 212 mg/ml with an osmotic pressure of less than 10 atmospheres, the solubility of tacrine in artificial gastric fluid is 168 mg/ml with an osmotic pressure of 19 atmospheres and the solubility of tacrine in artificial intestinal fluid is 205 mg/ml with an osmotic pressure of 18 atmospheres. This data leads-away from providing a dosage form comprising tacrine because of the much higher osmotic pressure of the environment of the gastrointestinal tract, combined with the therapeutic dose required, and the unknown and variable osmotic pressure of the gastrointestinal tract, which often result from fluid fluctuation, digestion and absorption in the gastrointestinal tract. This invention enhances tacrine osmotic pressure by augmenting tacrine's osmotic pressure by 20 atmospheres to effect the delivery at a controlled rate of tacrine from the dosage form.

Example 4

The dosage form according to Example 3 wherein a therapeutic composition comprising 1 to 125 mg of tacrine is overcoated as a pulsed dose on the exterior surface of the semipermeable wall.

Example 5

An osmotic dosage form possessing a length greater than its cross-section is manufactured as a caplet for delivering substantially 100% of its tacrine. The osmotic caplet comprises an internal coat to improve the structure and the performance of the osmotic caplet and to provide tacrine in a controlled-programmable rate. An osmotic caplet is manufactured by blending 9.0 g of tacrine hydrochloride monohydrate, 12.9 g sodium carboxymethylcellulose of 90,000 molecular weight, and 6.60 g of sorbitol in a roll mill for 15 minutes. Next, 1.20 g of poly(vinylpyrrolidone) of 35,000 molecular weight dissolved in 10 ml of ethyl alcohol is added to the blend and granulation continued for 5 to 8 minutes. The wet granulation is screened through a 20-mesh screen and dried over night for 18 hours at 25° C. Then, 0.30 g of magnesium stearate is added to the dry granules and blended for an additional 5 minutes to yield a tacrine composition.

Next, a displacement composition is prepared by blending 4,112.5 g of sodium carboxymethylcellulose of 700,000 molecular weight, 2,100.0 g of sodium chloride, and 350.0 g of hydroxypropylcellulose of 60,000 molecular weight in a fluid bed granulator, and all the ingredients blended for 5 to 10 minutes. Then, a granulation fluid comprising 350.0 g of hydroxypropylmethylcellulose of 11,200 molecular weight as a 5% aqueous solution is added to the fluid bed. The granulation fluid is added slowly by spraying it onto the fluidizing bed. Fluidization is continued for an additional 15 minutes. Next, the granules are passed through a 16-mesh screen.

Next, a number of solid caplets are prepared by pressing tacrine compositions comprising 108.00 mg of tacrine hydrochloride monohydrate, 154.80 mg of sodium carboxymethylcellulose, 79.20 mg of sorbitol, 14.40 mg of poly(vinylpyrrolidone) and 3.60 mg of magnesium stearate, against the displacement composition comprising 84.60 mg of sodium carboxymethylcellulose, 43.20 mg of sodium chloride, 7.20 mg of hydroxypropylcellulose, 7.20 mg of hydroxypropylmethylcellulose, and 0.36 mg of magnesium stearate compositions. Then, the tacrine composition and the displacement composition are added separately to the cavity of a caplet mold and the two compositions compressed into a two-layer core that is coated first with a subcoat composition comprising 70:30 hydroxypropylcellulose having a 80,000 molecular weight and hydroxypropylcellulose having a 9,600 molecular weight applied as an 8% solid aqueous solution. The coat is applied using a 12-inch (30-cm) pan coater. Next, a semipermeable membrane comprising 88:12 (wt:wt) mixture of cellulose acetate comprising a 39.8% acetyl content and polyethylene glycol of 4,000 molecular weight dissolved in 80/20 acetone methanol as 4% solid solution is coated as a semipermeable exterior wall over the interior subcoat. The semipermeable wall applied is 40.3 mg. Next, a 40 mil (1.01 mm) orifice is drilled through the tacrine end of the semipermeable wall and the internal subcoat for delivering tacrine from the caplet. The caplet prepared by this example comprises in the tacrine layer, that is a tacrine composition comprising 108.00 mg tacrine hydrochloride monohydrate, 154.80 mg of sodium carboxymethylcellulose of 90,000 molecular weight, 79.20 mg of sorbitol, 14.40 mg of poly(vinylpyrrolidone) and 3.60 mg of magnesium stearate; the displacement composition, an osmotic layer, comprises 84.60 mg of sodium carboxymethylcellulose of 700,000 molecular weight 43.20 mg of sodium chloride, 7.20 mg of hydroxypropylcellulose, 7.20 mg of hydroxypropylmethylcellulose and 0.36 mg of magnesium stearate; the subcoat comprises 8.26 mg of hydroxypropylcellulose and 3.54 mg of hydroxypropylmethylcellulose; and the semipermeable wall comprises 32.24 mg of cellulose acetate with a 39.8% acetyl content and 8.06 mg of polyethylene glycol having a 4000 molecular weight. The dosage caplet has a mean release rate of 10.37 mg/hr over 24 hours.

Example 6

The procedure of Example 5 is followed in this example, with the manufacturing conditions as described, except that in this example the tacrine composition comprises poly (ethylene oxide) having a 200,000 molecular weight as a replacement for the sodium carboxymethylcellulose, and the displacement layer comprises poly(ethylene oxide) having a 5,000,000 molecular weight that replaces the sodium carboxymethylcellulose.

Example 7

The procedure of Example 5 is followed in this example, with the manufacturing conditions as described, except that in this example, the tacrine composition comprises a poly (ethylene oxide) having a 100,000 molecular weight as a replacement for the sodium carboxymethylcellulose, the displacement layer comprises poly(ethylene oxide) having a 2,000,000 molecular weight that replaces the sodium carboxymethylcellulose, and an immediate or pulsed release dose of tacrine hydrochloride is coated onto the semipermeable wall, comprising 15 to 30 mg of tacrine.

Example 8

The procedure of Example 7 is followed to provide a dosage form comprising a pulsed-release dose of 15 to 30 mg of tacrine and an extended release dose of 85 to 150 mg of tacrine and 2 to 20 mg of selegiline.

Example 9

The procedure of Example 4 is followed in this example, with the manufacturing steps as set forth, except that in this example the tacrine composition comprises poly(ethylene oxide) of 300,000 molecular weight and the displacement composition comprises poly(ethylene oxide) of 7,800,000 molecular weight.

Example 10

A dosage form adapted, designed and shaped as an osmotic drug delivery device for oral administration to a patient having a neurological disease, is manufactured as follows: first, a drug granulation is made, by preparing a binder solution. The binder solution is prepared by dissolving 4,800 g of hydroxypropylmethylcellulose possessing a molecular weight of 11,200 and 1,600 g of poly (vinylpyrrolidone) having an average molecular weight of 40,000 in 73,600 g of water.

Next, 47,600 g of tacrine hydrochloride and 79,800 g of mannitol are sized using a 20 mesh screen. Then, the screened materials are added to a granulator bowl. The bowl is attached to the granulator and the granulation process initiated. Next, the dry powders are air suspended and mixed for 3 minutes. Then, the binder solution is sprayed onto powder to produce granules of tacrine and mannitol granulated with the binder ingredients. The processing conditions are as follows: a total solution spray rate of 900 g/minute, an inlet temperature of 65° C., and a process air flow of 1000 to 2500 m$^3$/hr.

After the 69,800 g of solution is sprayed, the granules are further processed by drying for 35 minutes. Next, the granules are removed from the granulator, and sized through an 8 mesh screen. Then, the granulation is transferred to a tumbler, and mixed with 4,200 g of crospovidone, crosslinked poly(vinylpyrrolidone), for 15 minutes. Next, 1,400 g of magnesium stearate is added to the tumbler and mixing continued for 2 minutes.

Next, the tacrine composition is compressed into tablets in a tablet press. First, 638 mg of the tacrine composition is added to the die cavity, then the composition is pressed under a pressure of approximately 1,000 pounds using a 0.436 inch (1.11 cm) standard round concave tool. The concentration of tacrine in the tablet is 170 mg.

The tablets then are coated with a semipermeable wall. The wall-forming composition comprises 1,898 g of cellulose acetate having a 32.0% acetyl content, and 100 g of polyethylene glycol having a molecular weight of 3350. The wall-forming composition is dissolved in acetone:water (88:12 wt:wt) cosolvent to provide a 4% solids solution. The wall-forming composition is sprayed onto and around the tablets in a coater.

Then, one 9 mil (0.227 mm) exit passageway is drilled through the semipermeable wall to connect the tacrine composition with the exterior of the dosage form. The residual coating solvent is removed by drying for at least 48 hours at 45° C. and 45% relative humidity. Next, dosage forms are dried for an additional 4 hours at 45° C. to remove excess moisture.

The dosage forms are divided into two groups: one group administrable as manufactured, and one group is provided with an overcoat of tacrine. The group provided with a pulsed-released tacrine overcoat consists of 1,600 g of tacrine hydrochloride, 360 g of hydroxypropylmethylcellulose possessing an average molecular weight of 11,200 and 400 g of polyethylene glycol of 3350 molecular weight. The pulse-releasable tacrine overcoat composition is dissolved in 8,000 g of water, heated to 37° C. to make 20% solids solution. The pulsed-releasable tacrine overcoat is applied by spray-coating in a coater. The dose of pulsed-releasable tacrine on each dosage form is 30 mg, and it is pulsed-released in from instantly to 30 minutes.

The dosage forms are coated with a color, tastemask outermost overcoat consisting of 975 g of white colorant dispersed in 6,525 g of water. The colorant is applied in a standard coater.

The dosage forms produced by this manufacture have the following composition: the tacrine drug composition comprises 34.0% tacrine hydrochloride, 57.0% mannitol, 3.0% hydroxypropylmethylcellulose possessing a 11,200 average molecular weight, 1.0% noncross-linked poly (vinylpyrrolidone) possessing a 40,000 molecular weight, 3.0% cross-linked poly(vinylpyrrolidone) of 1,000,000 molecular weight, and 1% magnesium stearate. The semipermeable wall comprises 95.0% cellulose acetate having a 32.0% acetyl content and 5% polyethylene glycol having a 3350 molecular weight. The dosage forms manufactured with the pulsed-released tacrine overcoat composition comprise 80.0% tacrine hydrochloride, 18.0% hydroxypropyl-methylcellulose of 11,200 average molecular weight and 20% polyethylene glycol of 3,350 molecular weight.

The dosage form is a pulsed-released, extended-released dosage form. The pulsed-released 30 mg dose is administered instantly to thirty minutes and the extended-released dose administered as follows: from 0 to 2 hours the dosage form released 20 to 50 mg of tacrine; from 0 to 8 hours the dosage form released 60 to 120 mg of tacrine; from 0 to 14 hours the dosage form released 110 to 170 mg of tacrine; and from 0 to 24 hours the dosage form release is equal to or greater than 170 to 200 mg of tacrine.

Example 11

The procedure of Example 10 is followed for manufacturing a dosage form comprising a pulsed-released dose of tacrine of 22.5 mg and an extended-release dose of 127.5 mg of tacrine.

Example 12

The procedure of Example 10 is followed for manufacturing a dosage form comprising a pulsed-released dose of 10 mg of selegiline and an extended-release dose of 85 mg of tacrine.

Example 13

The procedure of Example 10 is followed for manufacturing a dosage form comprising a pulsed-released dose of 5 mg of donepezil hydrochloride and an extended-release dose of 40 mg of tacrine hydrochloride.

Example 14

The procedure of Example 10 is followed for manufacturing a dosage form comprising 15 to 30 mg of a pulsed-released dose of tacrine and 85 to 170 mg of tacrine and 1,500 to 2,500 units of vitamin E extended-release dose.

Example 15

A tacrine extended-release dosage form is manufactured according to the above examples wherein the dose-kinetics of administration for a 200 mg dose of tacrine is as follows: 0 to 2 hours 10 to 25% delivered; 0 to 8 hours 30 to 60% delivered; 0 to 14 hours 55 to 85% delivered; and 0 to 24 hours 85 to 100% delivered to a patient orally in need of tacrine therapy.

Example 16

A drug delivery system is prepared according to the procedure of Example 9. The delivery systems are manufactured in this example with a cosmetic colorant overcoat formed from 975 g of Opadry No. YS-1-12660 dispersed in 6,525 g of water, and commercially available from Colorcon Inc, West Point, Pa. The color composition is sprayed onto and around the delivery systems in a coater. The overcoat of color also provides an improved surface for receiving an immediate release dose of tacrine to adhere to.

Next, the systems are coated with an immediate release tacrine coat that consists of 1,600 g of tacrine pharmaceutically acceptable salt, 300 g of hydroxypropylmethylcellulose possessing an 11,200 average molecular weight, and 40 g of polyethylene glycol having a 3,350 molecular weight. The immediate release tacrine outermost-overcoat composition is dissolved in 8,000 g of water heated to 37° C. to provide a 20% solids solution. The tacrine composition is applied by spraying in a standard coater. The dose of tacrine on an immediate release delivery system is 22.5 mg.

Finally, the dosage systems are coated with a second colored coat comprising the colorant, as identified above. The colorant is formed from a composition comprising 975 g of colorant in 6,525 g of water. The colorant is applied by spraying in a standard coater.

The dosage form produced by this manufacture comprises the following: the tacrine drug composition comprises 34% tacrine hydrochloride, the pharmaceutically acceptable salt, 57% mannitol, 3% hydroxypropylmethylcellulose possessing an 11,200 average molecular weight, 1.0% of poly(vinylpyrrolidone) of 40,000 average molecular weight, 3.0% g of crosslinked poly(vinylpyrrolidone) of 1,000,000 molecular weight, and 1% magnesium stearate. The wall comprises a semipermeable composition 95% cellulose acetate having a 32% acetyl content, and 5% polyethylene glycol of 3,350 molecular weight. The first color overcoat in contact with the exterior surface of the semipermeable wall comprises 100% colorant. The immediate release tacrine overcoat composition comprises 80% tacrine hydrochloride, 18% hydroxypropylmethylcellulose of 11,200 average molecular weight, and 2% polyethylene glycol of 3,350 molecular weight. The second color overcoat in contrast with the exterior, or outer surface of the immediate release tacrine dose comprises 100% colorant. The dosage form comprises a 9 mil (0.227 mm) passageway.

The dose release pattern from the dosage form is as follows: 15 to 38 mg in 0 to 2 hours, 45 to 90 mg in 0 to 8 hours, 82 to 128 mg in 0 to 14 hours, and 128 to 150 mg in 0 to 24 hours. The dose release rate expressed in percent is as follows: 10 to 25% in 0 to 2 hours, 30 to 60% in 0 to 8 hours, 55 to 85% in 0 to 14 hours, and 85 to 100% in 0 to 24 hours.

Example 17

The dosage form according to Example 9, wherein the tacrine in the dosage form is present with an additional or second adjunct drug for ameliorating neurological disease exhibiting a slowing of nerve impulse transmissions symptoms.

Example 18

The dosage form according to claim 17 wherein the adjunct drug is selected from the group consisting of monoaminopyridine, cytisine, diaminopyridine, physostigmine, ozacylic, aniracetam, bifemelane, phosphatidylserine, pramiracetam, fampridine, linopirdine, selegiline, estrogen, nimoldipine, propentofylline and relnacrine. The dose of adjunct anti-Alzheimer's drug in the dosage form is 100 ng to 500 mg, with a total dose of anti-Alzheimer's drug for two or more drugs equal to 200 ng to 500 mg.

METHOD OF USING THE INVENTION

This invention pertains further to the use of the dosage forms and the therapeutic compositions for the treatment of neurological diseases including Alzheimer's disease. The use of the invention comprises a method of orally administering to a patient having a neurological disease such as Alzheimer's disease an extended-release dosage form comprising 1 to 500 mg of tacrine administered at a dose rate 10 to 25% in 0 to 2 hours, 25 to 60% in 0 to 8 hours, 55 to 85% in 0 to 14 hours and 85 to 100% in 0 to 24 hours for the management of the neurological disease.

The invention pertains further to the use of a dosage form for delivering tacrine orally to the gastrointestinal tract of a patient in need of tacrine therapy, wherein the use comprises: (1) admitting an osmotic caplet orally into the patient, which caplet comprises: (a) 100 ng to 1,500 mg of tacrine composition; (b) a displacement composition for imbibing fluid to increase in volume and push the tacrine composition from the caplet; (c) a semipermeable wall that surrounds the tacrine and displacement compositions; (d) a passageway in the caplet for delivering the tacrine to the patient; (2) imbibing fluid through the semipermeable wall into the caplet; thereby; (3) delivering the tacrine to the patient to provide the needed therapy over an extended release to 24 hours. The use includes also the caplet wherein a subcoat comprising a hydrophobic composition surrounds the tacrine composition and the displacement composition. The use includes further the caplet wherein an overcoat comprising an immediate-release composition surrounds the semipermeable wall.

The invention pertains further to the use of a dosage form comprising a tacrine composition, wherein the dosage form comprises: (1) a tacrine composition comprising 10 ng to 1,200 mg of tacrine; (2) a wall comprising a semipermeable composition that surrounds the tacrine composition; (3) an exit in the dosage form for delivering the tacrine to a patient; (4) imbibing an exterior fluid into the dosage form to occupy space in the dosage form; and thereby deliver the tacrine orally to the patient at an extended release rate of 0.40 ng/hr to 50 mg/hr for an extended time up to 24 hours to provide the intended tacrine therapy.

In summary, it will be appreciated the present invention contributes to the tacrine dispensing art by providing an unexpected and unique dosage form that possesses a practical utility, and can administer tacrine at a metered extended-release rate up to 24 hours for preselected tacrine therapy. While the invention has been described and pointed out in detail with reference to operative embodiments thereof, it will be understood by those skilled in the art that various changes, modifications, substitutions and omissions can be made without departing from the spirit of the invention. It is intended therefore, that the invention embraces those equivalents within the scope of the claims which follow.

What is claimed is:

1. A method for treating Alzheimer's disease, wherein the method comprises administering orally to a patient having Alzheimer's disease a pulsed-release dose of tacrine for treating the disease and an extended-release dose of tacrine administered with a therapeutic member selected from the group consisting of aniracetam, bifemelane, phosphatidylserine, pramiracetam, physostigmine, fampridine, linopirdine, selegiline, nimodipine, propentofylline, alpha-tocopherol, estrogen, aminopyridine, cytisine, 1-hydroxy-tacrine, and donepezil, for treating the Alzheimer's disease.

2. A method for treating Alzheimer's disease wherein the method comprises administering orally to a patient having Alzheimer's disease a pulsed-release dose of tacrine for treating the disease administered with a therapeutic member selected from the group consisting of selegiline, alpha-tocopherol, 1-hydroxy-tacrine, and donepezil, and an extended-release dosage of tacrine, for treating the Alzheimer's disease, wherein the tacrine and said therapeutic member are present in combination in a dosage form.

3. A method for treating Alzheimer's disease wherein the method comprises administering orally to a patient having Alzheimer's disease a dose of tacrine administered with a dose of a member selected from the group consisting of selegiline, alpha-tocopherol, 1-hydroxy-tacrine, and donepezil for treating the disease, and an extended release dose of a therapeutic member selected from the group consisting of aniracetam, tacrine, bifemelane, phosphatidylserine, pramiracetam, physostigmine, fampridine, linopirdine, selegiline, nimodipine, propentofylline, alpha-tocopherol, estrogen, aminopyridine, cytisine, 1-hydroxy-tacrine, and donepezil, for treating the Alzheimer's disease.

4. A method for treating a neurological disease wherein the method comprises administering orally to a patient having a neurological disease a dose of tacrine for treating the disease administered at a dose corresponding to the following therapeutic program: from 20 to 50 mg of tacrine in 0 to 2 hours, from 60 to 120 mg in 0 to 8 hours, from 110 to 170 mg in 0 to 14 hours, and from 170 to 200 mg in 0 to 24 hours, accompanied by a therapeutic member selected from the group consisting of aniracetam, bifemelane, phosphatidylserine, pramiracetam, physostigmine, fampridine, linopirdine, selegiline, nimodipine, estrogen, propentofylline, alpha-tocopherol, aminopyridine, cytisine, 1-hydroxy-tacrine, and donepezil, for treating the neurological disease.

5. A method for treating a neurological disease wherein the method comprises administering orally to a patient having a neurological disease a pulsed-release dose of tacrine for treating the disease accompanied by the administration of a therapeutically effective dose of a member selected from the group consisting of selegiline, alpha-tocopherol, 1-hydroxy-tacrine, and donepazil, and an extended-release dose of tacrine administered according to the following therapeutic pattern: from 0 to 2 hours the administered dose is 10 to 25%, from 0 to 8 hours the administered dose is 30 to 60%, from 0 to 14 hours the administered dose is 55 to 85%, and from 0 to 24 hours the administered dose is greater than 85% of the tacrine, accompanied by a dose of a member selected from the group consisting of aniracetam, bifemelane, phosphatidylserine, pramiracetam, physostigmine, fampridine, linopirdine, selegiline, nimodipine, estrogen, propentofylline, alpha-tocopherol, aminopyridine, cytisine, 1-hydroxy-tacrine, and donepezil, for the treatment of the neurological disease.

6. A dosage form comprising a therapeutically effective dose of a member selected from the group consisting of tacrine and a pharmaceutically acceptable salt that is administered in from instantly to thirty minutes accompanied by a therapeutically effective dose of a member selected from the group consisting of selegiline, alpha-tocopherol, 1-hydroxy-tacrine, and donepezil for treating a neurological disease, and an extended-release therapeutically effective dose of a member selected from the group consisting of tacrine and a pharmaceutically acceptable salt that is administered from thirty minutes to 24 hours accompanied by a therapeutically effective dose of a member selected from the group consisting of aniracetam, bifemelane, phosphatidylserine, pramiracetam, physostigmine, fampridine, linopirdine, selegiline, nimodipine, propentofylline, alpha-tocopherol, estrogen, aminopyridine, cytisine, 1-hydroxy-tacrine, and donepezil for treating the neurological disease.

7. A caplet for delivering a therapeutically effective composition orally to an Alzheimer's patient, wherein the caplet comprises:

(a) a therapeutic composition comprising 100 ng to 500 mg of tacrine and a therapeutic member selected from the group consisting of aniracetam, bifemelane, phosphatidylserine, pramiracetam, physostigmine, fampridine, linopirdine, selegiline, nimodipine, propentofylline, alpha-tocopherol, estrogen, aminopyridine, cytisine, 1-hydroxy-tacrine, and donepezil for treating the Alzheimer's patient;

(b) an expandable composition that imbides fluid and increases in volume for displacing the therapeutic composition from the caplet;

(c) a wall comprising a composition permeable to fluid and impermeable to the therapeutic composition that surrounds the therapeutic composition;

(d) an overcoat on the surface of the caplet comprising a therapeutically effective dose of a member selected from the group consisting of selegiline, tacrine alpha-tocopherol, 1-hydroxy-tacrine, and donepezil for treating the Alzheimer's patient; and, (e) a passageway in the wall for delivering the therapeutic composition from the caplet to the patient.

8. A dosage form for delivering a therapeutically effective composition orally to the gastrointestinal environment of an Alzheimer's patient, wherein the dosage form comprises:
   (a) a therapeutic composition comprising 100 ng to 500 mg of a member selected from the group consisting of tacrine and tacrine pharmaceutically acceptable salt, and a therapeutically effective dose of a therapeutic member selected from the group consisting of aniracetam, bifemelane, phosphatidylserine, pramiracetam, physostigmine, fampridine, linopirdine, selegiline, nimodipine, propentofylline, alpha-tocopherol, estrogen, aminopyridine, cytisine, 1-hydroxy-tacrine, and donepezil for treating Alzheimer's disease,
   (b) a wall comprising a semipermeable composition permeable to gastrointestinal fluid and impermeable to the therapeutic composition that surrounds the therapeutic composition;
   (c) an overcoat on the wall comprising a therapeutically effective dose of a member selected from the group consisting of selegiline, tacrine, alpha-tocopherol, 1-hydroxy-tacrine, and donepezil;
   (d) an exit in the dosage form wall for delivering therapeutic composition to the patient; and,
   (e) wherein when the dosage form is administered to an Alzheimer's patient, the dosage form delivers the therapeutic composition over a 24 hour period at a therapeutic rate to slow the progression of Alzheimer's disease in the patient.

9. An osmotic dosage form for delivering tacrine to an Alzheimer's patient's gastrointestinal tract, wherein the dosage form comprises:
   (a) a tacrine composition comprising 108 mg of tacrine hydrochloride, 154.80 mg of sodium carboxymethylcellulose, 79.20 mg of sorbitol, 14.40 mg of poly(vinylpyrrolidone), and 3.60 mg of magnesium stearate;
   (b) a displacement composition comprising 84.60 mg of sodium carboxymethylcellulose, 43.20 mg of sodium chloride, 7.20 mg of hydroxypropylcellulose, 7.20 mg of hydroxypropylmethylcellulose, and 0.36 mg of magnesium stearate, that develops an osmotic pressure greater than the gastrointestinal tract;
   (c) a wall that surrounds the tacrine composition and the displacement composition, said wall comprising an 88:12 (wt:wt) mixture of cellulose acetate and polyethylene glycol; and,
   (d) an exit passageway in the wall that connects the tacrine composition with the exterior of the dosage form for delivering tacrine over 24 hours.

10. A dosage form for delivering tacrine to an Alzheimer's patient, wherein the dosage form comprises:
    (a) a tacrine composition comprising 34% tacrine, 57% mannitol, 3% hydroxypropylmethylcellulose, 1% noncrossed-linked poly(vinylpyrrolidone), 3% crosslinked poly(vinylpyrrolidone), and 1% magnesium stearate,
    (b) a wall comprising 95% cellulose acetate and 5% polyethylene glycol that surrounds the tacrine composition; and,
    (c) an exit through the wall for delivering tacrine from the dosage form.

11. A dosage form for delivering tacrine according to claim 10, wherein an overcoat is coated onto the wall, which overcoat comprises 80% tacrine, 18% hydroxypropylmethylcellulose and 2% polyethylene glycol.

12. A dosage form for delivering tacrine according to claim 10, wherein the tacrine is a member selected from the group consisting of tacrine base, tacrine salt, tacrine hydrochloride, tacrine hydrobromide, tacrine sulfate, tacrine phosphate, tacrine lactate, tacrine citrate, tacrine tartrate, tacrine malate, tacrine maleate, tacrine fumarate, tacrine ascorbate, tacrine gluconate, tacrine asparate, tacrine salicylate, tacrine edisylate, tacrine laurate, tacrine palmitate, tacrine nitrate, tacrine borate, tacrine acetate and tacrine oleate.

13. A dosage form for delivering a therapeutic composition to an Alzheimer's patient, wherein the dosage form comprises:
    (a) a therapeutic composition comprising 100 ng to 500 mg of a member selected from the group consisting of tacrine and its pharmaceutically acceptable salt, and a therapeutically effective dose comprising member selected from the group consisting of aniracetam, bifemelane, phosphatidylserine, pramiracetam, physostigmine, fampridine, linopirdine, selegiline, nimodipine, estrogen, propentofylline, alpha-tocopherol, aminopyridine, cytisine, 1-hydroxy-tacrine, and donepezil; 2 to 60 wt % of an osmotically active agent, 0.25 to 15 wt % of a poly (vinylpyrrolidone), 0 to 20 wt % of a cellulose ether, and 0.01 to 10 wt % of a lubricant, with the weight of all components in the composition equal to 100 wt %;
    (b) a wall that surrounds the composition, said wall permeable to fluid;
    (c) an overcoat on the wall comprising a therapeutically effective dose of a member selected from the group consisting of selegiline, tacrine, alpha-tocopherol, 1-hydroxy-tacrine, and donepezil indicated for the management of Alzheimer's disease; and,
    (d) an exit passageway in the wall that connects the therapeutic composition with the exterior of the dosage form for delivering the therapeutic composition over 24 hours to the patient for the management of Alzheimer's disease.

14. A caplet for delivering a therapeutic composition orally to an Alzheimer's patient, for the management of Alzheimer's disease, wherein the caplet comprises:
    (a) a therapeutic composition comprising 10 ng to 500 mg of a member selected from the group consisting of tacrine and its pharmaceutically acceptable salt, and a therapeutically effective dose of a member selected from the group consisting of aniracetam, bifemelane, phosphatidylserine, pramiracetam physostigmine, fampridine, linopirdine, selegiline, nimodipine, estrogen, propentofylline, alpha-tocopherol, aminopyridine, cytisine, 1-hydroxy-tacrine, and donepezil;
    (b) a subcoat comprising a hydrophilic composition that surrounds the therapeutic composition;
    (c) a wall comprising a semipermeable composition that surrounds the subcoat;
    (d) a passageway in the caplet for delivering the therapeutic composition; and
    (e) an overcoat that surrounds the wall comprising 1 to 125 mg of a member selected from the group consisting of tacrine and its pharmaceutically acceptable salt, accompanied by a therapeutically effective dose of a member selected from the group consisting of selegiline, alpha-tocopherol, 1-hydroxy-tacrine, and donepazil, indicated for the management of Alzheimer's disease.

* * * * *